United States Patent

Posner et al.

[11] Patent Number: 5,932,591
[45] Date of Patent: Aug. 3, 1999

[54] C₃ SUBSTITUTED TRIOXANES USEFUL AS ANTIPARASITIC DRUGS

[75] Inventors: Gary H. Posner; Jared N. Cumming; Soon Hyung Woo, all of Baltimore, Md.

[73] Assignee: Johns Hopkins University, Baltimore, Md.

[21] Appl. No.: 08/758,661

[22] Filed: Dec. 2, 1996

[51] Int. Cl.⁶ ...................... A61K 31/335; C07D 323/06
[52] U.S. Cl. .......................... 514/314; 514/444; 514/450; 514/461; 546/152; 549/60; 549/368; 549/429
[58] Field of Search .................... 549/368, 355, 549/60, 429; 514/314, 444, 461, 355; 546/152

[56] References Cited

U.S. PATENT DOCUMENTS

| | | | |
|---|---|---|---|
| 4,977,174 | 12/1990 | Stein | 514/382 |
| 5,057,501 | 10/1991 | Thornfeldt | 514/53 |
| 5,578,637 | 11/1996 | Lai | 514/450 |
| 5,672,624 | 9/1997 | Posner | 514/450 |

OTHER PUBLICATIONS

Cope et al., Cyclic Polyolefins, . . . Cyclooctatetra–enes, J. Am. Chem. Soc. (1955) vol. 77, pp. 4939–4940.
Desjardins, et al., Quantitative Assessment . . . Technique, Antimicrobial Agents and Chemotherapy, Dec. 1979, pp. 710–718.
Milhous et al., In Vitro Activities . . . Antimalarial Drugs, Antimicrobial Agents and Chemotherapy, Apr. 1985, pp. 525–530.
Carmichael et al., Evaluation of a . . . Testing, Cancer Research 47, Feb. 15, 1987, pp. 936–942.
Fraser et al., Is Uracil . . . Treatment?, Biochemical & Biophysical Research Communications, vol. 135, No. 3, 1986, Mar. 28, 1986, pp. 886–893.
Posner, et al., Further Evidence . . . Like Artemisinin, J. of Medicinal Chemistry, vol. 38, No. 13, pp. 2273–2275.
Jiang et al., Antimalarial Activity of Mefloquine and Qinghaosu, The Lancet, Aug. 7, 1982, pp. 285–288.
Bruce–Chwatt, Qinghaosu: a new antimalarial, British Medical Journal, vol. 284, Mar. 13, 1982, pp. 767–768.
Klayman, Qinghaosu (Artemisinin): An Antimalarial Drug from China, Science, vol. 228, May 31, 1985, pp. 1049–1055.

Miyashi et al., Evidence for a Chair Cyclohexane 1,4–Radical Cation . . . of 2,5–Diaryl–11,5–hexadienes, J. Am. Chem. Soc. 1988, 110, pp. 3676–3677.
Miyashi et al., Photoinduced electron–transfer reactions of the cope and related systems, Pure & Appl. Chem., 1990, vol. 62, No. 8, pp. 1531–1538.
Takahashi et al., Electron–Transfer . . . 2,6–Diarylhepta–1, 6–dienes, Tetrahedron Letters, 1994, vol. 35, No. 23, pp. 3953–3956.
Hudson, Atovaquone—A Novel Broad–spectrum Anti–infective Drug, Parasitology Today, vol. 9, No. 2, 1993, pp. 66–68.
Schmid et al., Total Synthesis of Qinghaosu, J. Am. Chem. Soc., 1983, 105, pp. 624–625.
Posner et al., U.S. Patent Appln. No. 08/701,423, filed Aug. 22, 1996.
Posner et al., Tetrahedron Letters 37:815–818 (1996).
Posner et al., Tetrahedron Letters 37:7225–7228 (1996).
Avery et al., J. Med Chem. 39: 2900–2906 (1996).
Posner et al., Heteroatom Chemistry 6: 105–116 (1995).
Posner et al., J. Amer. Chem. Soc. 118:3537–3538 (1996).

*Primary Examiner*—Johann Richter
*Assistant Examiner*—Jane C. Osweicki
*Attorney, Agent, or Firm*—Cushman Darby & Cushman IP Group of Pillsbury Madison & Sutro

[57] ABSTRACT

Novel biologically-active 3-substituted trioxanes of the formula

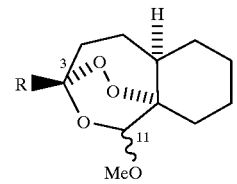

wherein R represents a substituted alkyl or aryl group of 1–20, preferably 1–12, carbon atoms, and methods for the use of biologically-active 3-substituted trioxanes of this formula as antiparasitic agents, particularly for the treatment of malaria.

13 Claims, No Drawings

C₃ SUBSTITUTED TRIOXANES USEFUL AS ANTIPARASITIC DRUGS

The invention described and claimed herein was made in part under a grant from the National Institutes of Health, NIH-AI-34885. The Government has certain rights in the invention.

BACKGROUND OF THE INVENTION

1. Field of the Invention

The present invention relates to novel biologically-active 3-substituted trioxanes and to their use as antiparasitic agents, particularly in malaria.

2. Description of the Related Art

The trioxane drug artemisinin is an active anti-malarial constituent of the herb *Artemisia annua* L., Compositae. The herb has been known in China for almost 2000 years. Artemisinin was first isolated in 1972 and shown to be a sesquiterpene lactone with a peroxide moiety (1). The molecular structure was first reported in 1983 (2) and is shown in the following formula:

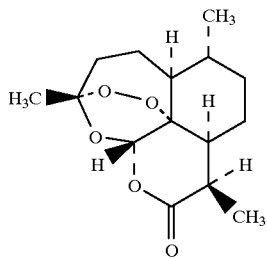

Several investigators have reported on the anti-malarial activity of artemisinin (3–5), and reviews of the chemistry, pharmacology and clinical applications of artemisinin have been published (6–8).

In addition to artemisinin, a number of related synthetic organic endoperoxides have been developed which have antimalarial activity. Saturated and unsaturated bicyclic endoperoxide compounds with antiparasitic/antimalarial activity are disclosed in U.S. application Ser. Nos. 08/562,275 and 08/701,423 (both of which are hereby incorporated herein by reference), and 1,2,4 trioxane analogs of Artemisinin have been described (9). Avery et al. (10) described 3-substituted Artemisinin analogs, and noted that substitution with branched hydrocarbons lowered antimalarial potency appreciably.

Biological evaluation of these compounds indicates that a number of them are effective nontoxic antiparasitic agents. However, parasitic infections, particularly malaria, remain a serious and widespread public health problem, and concern exists about possible side effects of compounds developed to date. For example, neurotoxicity has been seen in rats which were administered high doses of artemether and in mouse neuroblastoma cells treated with dihydroartemesisin (11). For this reason, a need remains for the development of improved therapeutic agents for prevention and treatment.

SUMMARY OF THE INVENTION

It is an object of the present invention to provide compounds and methods for treating parasitic infections such as malaria and cerebral toxoplasmic encephalitis. To accomplish this object, the invention provides 3-substituted trioxanes of the formula

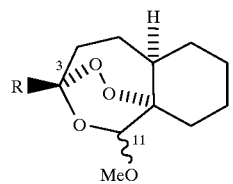

wherein R represents a substituted or unsubstituted alkyl or aryl group of 1–20, preferably 1–12, carbon atoms. It will be appreciated by one of skill in the art that this structure contains an asymmetric center at position 11 and that the MeO group in position 11 may be in either an α or β orientation. Of the two orientations, β is the preferred form of the invention.

The term "aryl" according to the invention, is intended to mean a compound or substituent having at least one aromatic C-ring, and is particularly intended to include phenyl, biphenyl, and heterocyclic aromatic rings of 5–6 atoms or bicyclic rings of up to 10 atoms which have at least one nitrogen, sulphur or oxygen atom. The term "alkyl" according to the invention, is intended to mean a saturated aliphatic hydrocarbon group, particularly a straight or branched carbon chain of 1–12 carbon atoms. The term "alkenyl" according to the invention, is intended to mean an unsaturated aliphatic hydrocarbon group, particularly a straight or branched carbon chain of 1–12 carbon atoms.

In one prefered embodiment of the invention, R represents an aryl or functionalized aryl which is a substituted or unsubstituted phenyl or biphenyl group. Particularly preferred in this regard are substituents which are unsubstituted or have substitutions in the para position, for example Ph, p-PhPh, p-FPh, p-F-o-MePh, p-MeOPh, p-(HOCH₂)Ph, p-formyl-Ph, p-diethylaminomethyl-Ph, and p-CF₃Ph. Another particularly prefered substituent is m,m'-(HOCH₂)₂Ph. Preferred embodiments of the invention are also considered to include combinations of two or more potentiating groups, e.g. wherein the phenyl group is substituted with two or more of substituents F–, MeO–, HOCH₂–, and so forth.

In another prefered embodiment of the invention, R represents a heteroaryl or functionalized heteroaryl group, for example a furyl, thienyl, or quinolyl group. Particularly preferred substituents in this regard include 2-furyl, 2-thienyl, and 3-quinolyl.

In another embodiment of the invention, R represents a substituted or unsubstituted alkyl or alkenyl group, particularly a mono- or polyfluoroalkyl group. Examples of substituents of this embodiment are fluoromethyl, ethyl, vinyl, (CH₃)₂CHCH₂CH₂, trifluoromethyl, and (3,3,3)-trifluoropropyl.

These compounds can be used according to a further embodiment of the invention for treatment of malaria and other parasitic infections by the administration of effective dosages to persons in need of such treatment. Suitable dosages are expected to be in the range of about 30 mg to 5 gm, preferably about 300 to 1000 mg administered over a period of 2–5 days.

These and other objects of the invention can be accomplished using the methods set forth in the following detailed examples.

DETAILED DESCRIPTION OF THE INVENTION

Experimental

General

Unless otherwise noted: Reactions were run in flame-dried round-bottomed flasks under an atmosphere of ultra high purity (UHP) argon. Diethyl ether (ether) and tetrahydrofuran (THF) were distilled from sodium benzophenone ketyl prior to use. Methylene chloride ($CH_2Cl_2$) was distilled from calcium hydride prior to use. All other compounds were purchased from Aldrich Chemical Company and used without further purification. Analytical thin-layer chromatography (t.l.c.) was conducted with Silica Gel 60 $F_{254}$ plates (250 μm thickness, Merck). Column chromatography was performed using short path silica gel (particle size<230 mesh), flash silica gel (particle size 400–230 mesh), or FLORISIL® (200 mesh). Yields are not optimized. High performance liquid chromatography (HPLC) was carried out with a Rainin HPLX system equipped with two 25 mL/min preparative pump heads using Rainin Dynamax 10 mm×250 mm (semi-preparative) columns packed with 60 Å silica gel (8 μm pore size), either as bare silica or as C-18-bonded silica. Melting points were measured using a Mel-Temp metal-block apparatus and are uncorrected. Nuclear magnetic resonance (NMR) spectra were obtained either on a Varian XL-400 spectrometer, operating at 400 MHz for $^1H$ and 100 MHz for $^{13}C$ or on a Varian XL-500 spectrometer, operating at 500 MHz for $^1H$ and 125 MHz for $^{13}C$. Chemical shifts are reported in parts per million (ppm, δ) downfield from tetramethylsilane. Splitting patterns are described as singlet (s), doublet (d), triplet (t), quartet (q), multiplet (m), and broad (b). Infrared (IR) spectra were obtained using a Perkin-Elmer 1600 FT-IR spectrometer. Resonances are reported in wavenumbers ($cm^{-1}$). Low resolution (LRMS) and high resolution (HRMS) mass spectra were obtained on a VG Instruments 70-S spectrometer run at 70 eV for electronic ionization (EI) and run with ammonia ($NH_3$) as a carrier for chemical ionization (CI). Combustion analyses were conducted by Atlantic Microlab (Norcross, Ga.). A preliminary report of several of the synthetic schemes described below has been published (12).

General Procedure 1: Trioxane Formation by Singlet Oxygenation

A sulfonation (3-necked) flask was fitted with a gas inlet line, an outlet line with stopcock, and a septum. To this flask was added solid methylene blue (ca. 5 mg) followed by a solution of the starting ketone (1.0 equivalents) in $CH_2Cl_2$ (0.01 M). The resulting solution was cooled to −78° C. while UHP oxygen passed through a drying column was bubbled (ca. 1 mL/s) through the solution. The reaction mixture was then irradiated with UV light (medium pressure Hg lamp) with continuous $O_2$ bubbling just until t.l.c. analysis showed >95% consumption of starting material. After irradiation, an argon source was introduced through the septum, the outlet stopcock was closed, and the gas inlet line was replaced with a stopper. To this reaction mixture, still at −78° C., was then added by cannula a −78° C. solution of t-$BuMe_2SiOTf$ (1.1 equivalents) in $CH_2Cl_2$ (0.50 M). The resulting solution was stirred for 8 h at −78° C. At that time, the reaction was quenched by addition via syringe over 2 min of $Et_3N$ (neat, 3.3 equivalents). The mixture was allowed to warm to room temperature (r.t.) slowly over at least 3 h and was then concentrated under reduced pressure to ca. 1 mL total volume.

General Procedure 2: Desilylation by Fluoride Ion

To a solution of starting silyl ether (1.0 equivalents) in THF (0.33 M) at 0° C. was added a 0° C. solution of $Bu_4NF$ (monohydrate, 1.5 equivalents) in THF (0.67 M). The resulting solution was stirred at 0° C. until the starting material was consumed. The reaction was quenched with $H_2O$ (3 mL) and then diluted with appropriate volumes of ether and $H_2O$. The organic phase was separated, and the aqueous phase was extracted with appropriate volumes ether. The organic portions were combined, washed with saturated aqueous NaCl, dried over anhydrous $MgSO_4$, filtered, and concentrated under reduced pressure.

Synthesis of $C_3$-Aryl Trioxanes $C_3$-Aryl Trioxanes were synthesized according to the following general scheme:

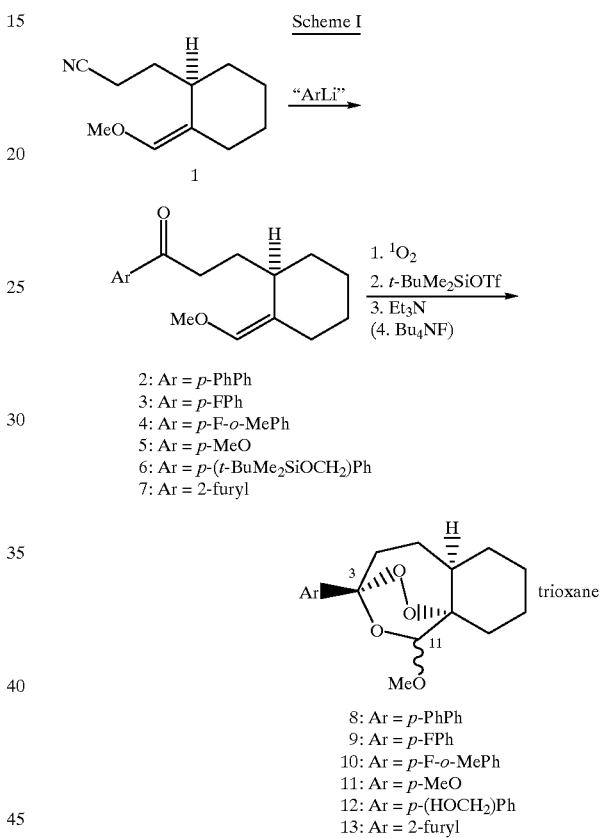

4-Biphenyl Ketone 2

To a solution of 4-bromobiphenyl (770 mg, 3.30 mmol) in ether (4 mL) at 0° C. was added n-BuLi (2.5 mL, 1.25 M in hexanes, 3.1 mmol) via syringe. This solution was stirred at 0° C. for 5 min, then warmed to r.t. and stirred for 1 h. The resulting greenish grey turbid mixture wa added dropwise via cannula (without cooling) to a −78° C. solution of nitrile 1 (370 mg, 2.06 mmol) in ether (14 mL). The reaction mixture turned bright orange and fumed extensively during the addition. The mixture was stirred at −78° C. for 5 min, then warmed to r.t. and stirred for 3 h. At that time, the reaction was quenched with $H_2O$ (3 mL) and then diluted with ether (50 mL) and $H_2O$ (50 mL). The organic phase was separated, and the aqueous phase was extracted with ether (50 mL×2). The organic portions were combined, washed with saturated aqueous NaCl, dried over anhydrous $MgSO_4$, filtered, and concentrated under reduced pressure. The crude product was purified by column chromatography (20 g short path, 1%→10% EtOAc/hexane) to give the desired product (282 mg, 2.53 mmol, 41%) as a light pink solid: m.p.=

93–94.5° C.; $^1$H NMR (400 MHz, CDCl$_3$) δ 8.02 (m, 2H), 7.67 (m, 2H), 7.62 (m, 2H), 7.46 (m, 2H), 7.39 (m, 1H), 5.81 (d, J=2.0 Hz 1H), 3.43 (s, 3H), 3.03–2.88 (m, 3H), 2.03 (m, 2H), 1.85–1.73 (m, 3H), 1.64 (m, 1H); 1.59–1.49 (m, 3H), 1.22 (m, 1H); $^{13}$C NMR (100 MHz, CDCl$_3$) δ 200.2, 145.1, 140.3, 139.8, 135.9, 128.8, 128.5, 128.0, 127.1, 126.9, 118.9, 59.0, 36.8, 32.6, 31.6, 28.2, 26.4, 25.8, 21.6; IR (CHCl$_3$) 3032, 3012, 2931, 2856, 1678, 1605, 1238, 1449, 1404, 1124 cm$^{-1}$; LRMS (EI, rel intensity) submitted; HRMS (EI) m/z submitted.

C$_3$-(4-Biphenyl) Trioxanes 8

4-Biphenyl ketone 2 (190 mg, 0.565 mmol) was treated according to General Procedure 1 (irradiation for 20 min). The crude reaction mixture was purified by column chromatography (ca. 15 g FLORISIL®, 1%→10% EtOAc/hexanes) to give C$_{11\alpha}$-OMe trioxane 8a (90 mg, 0.24 mmol, 43%) and C$_{11\beta}$-OMe trioxane 8b (45 mg, 0.324 mmol, 22%).

Further purification of 8a by HPLC (silica, 85% CH$_2$Cl$_2$/hexanes, 2.5 mL/min, 274 nm, R$_t$=15.8 min) afforded a white solid: $^1$H NMR (400 MHz, CDCl$_3$) δ 7.60 (m, 6H), 7.43 (m, 2H), 7.34 (m, 1H), 5.20 (s, 1H), 3.64 (s, 3H), 2.87 (ddd, J=14.4, 13.2, 3.6 Hz, 1H), 2.43 (m, 1H), 2.33 (ddd, J=14.8, 4.8, 2.4 Hz, 1H), 1.90 (m, 1H), 1.84–1.68 (m, 4H), 1.64 (m, 1H), 1.33–1.18 (m, 4H); $^{13}$C NMR (100 MHz, CDCl$_3$) δ 141.5, 140.5, 139.4, 128.7, 127.4, 127.1, 126.8, 125.8, 103.9, 96.1, 83.6, 56.0, 45.4, 37.5, 33.4, 32.5, 27.2, 25.3, 23.1; IR (CHCl$_3$) 3032, 3012, 2934, 2863, 1600, 1488, 1451, 1348, 1099, 1006 cm$^{-1}$.

Further purification of 8b by HPLC (silica, 3% EtOAc/hexanes, 3 mL/min, 274 nm, Rt=9.9 min) afforded a white solid: m.p.=146–147° C.; $^1$H NMR (400 MHz, CDCl$_3$) δ 7.60 (m, 6H), 7.43 (m, 2H), 7.35 (m, 1H), 5.17 (d, J=1.2 Hz, 1H), 3.67 (s, 3H), 2.82 (ddd, J=14.8, 13.2, 3.6 Hz, 1H), 2.36 (ddd, J=14.4, 4.4, 3.2 Hz, 1H), 2.05–1.90 (m, 2H), 1.82–1.62 (m, 7H), 1.31 (dt, J$_d$=4.8 Hz, J$_t$=13.6 Hz, 1H) overlapping 1.24 (m, 1H); $^{13}$C NMR (100 MHz, CDCl$_3$) δ 141.6, 140.6, 139.7, 128.7, 127.4, 127.1, 126.9, 125.7, 105.1, 105.0, 83.8, 57.2, 47.5, 39.1, 35.7, 30.8, 26.9, 25.1, 23.9; IR (CHCl$_3$) 3035, 3011, 2933, 2862, 1600, 1487, 1447, 1219, 1138, 1103 cm$^{-1}$; Anal. calcd for C$_{23}$H$_{26}$O$_4$; C 75.37, H 7.16, found: C 74.90, H 7.19. Note that this combustion analysis rules out the deoxytrioxane product, anal. calcd for C$_{23}$H$_{26}$O$_3$; C 78.80, H 7.49.

p-Fluorophenyl Ketone 3

To a solution of nitrile 1 (900 mg, 5.02 mmol) in ether (45 mL) at 0° C. was added via syringe p-fluorophenylmagnesium bromide (5.0 mL, 2.0 M solution in ether 10 mmol). The resulting turbid mixture was stirred at 0° C. for 5 min then warmed to r.t. and stirred for 6 h. At that time, the reaction was quenched with H$_2$O (3 mL) and then diluted with ether (25 mL) and H$_2$O (25 mL). The organic phase was separated, and the aqueous phase was extracted with ether (80 mL×2). The organic portions were combined, washed with saturated aqueous NaCl, dried over anhydrous MgSO$_4$, filtered, and concentrated under reduced pressure. The crude product was purified by column chromatography (30 g short path, 1%→10% EtOAc/hexane) to give the desired product (700 mg, 2.53 mmol, 50%) as a pale yellow oil: $^1$H NMR (400 MHz, CDCl$_3$) δ 7.97 (m, 2H), 7.11 (m, 2H), 5.79 (d, J=2.0 Hz, 1H), 3.41 (s, 3H), 2.97–2.81 (m, 3H), 2.00 (m, 2H), 1.82 (m, 1H), 1.74 (m, 2H), 1.65 (m, 1H), 1.53 (m, 3H), 1.21 (m, 1H); $^{13}$C NMR (100 MHz, CDCl$_3$) δ 199.0, 165.3 (d, J=253 Hz), 140.4, 133.7 (d, J=3.0 Hz), 130.4 (d, J=9.1 Hz), 118.8, 115.3 (d, J=22.0 Hz), 59.0, 36.6, 32.5, 31.6, 28.2, 26.4, 25.7, 21.6.

C$_3$-(p-Fluoro)phenyl Trioxanes 9 p-Fluorophenyl ketone 3 (270 mg, 0.977 mmol) was treated according to General Procedure 1 (irradiation for 15 min). The crude reaction mixture was purified by column chromatography (ca. 20 g FLORISIL®, 1%→10% EtOAc/hexanes) go give C$_{11\alpha}$-OMe trioxane 9a (60 mg, 0.19 mmol, 20%) and C$_{11\beta}$-OMe trioxane 9b (100 mg, 0.324 mmol, 33%).

Further purification of 9a by HPLC (C-18, 10% water/methanol, 3 mL/min, 260 nm, Rt=9.3 min) afforded a white solid: m.p.=97–98° C.; $^1$H NMR (400 MHz, CDCl$_3$) δ 7.54 (m, 2H), 7.03 (m, 2H), 5.17 (s, 1H), 3.61 (s, 3H), 2.83 (ddd, J=14.4, 13.2, 3.6 Hz, 1H), 2.41 (m, 1H), 2.25 (ddd, J=14.4, 4.8, 2.4 Hz, 1H), 1.89 (m, 1H), 1.82–1.70 (m, 4H), 1.62 (m, 1H), 1.30–1.15 (m, 4H); $^{13}$C NMR (100 MHz, CDCl$_3$) δ 162.8 (d, J=246 Hz), 136.4 (d, J=3.0 Hz) 127.4 (d, J=8.3 Hz), 115.0 (d, J=22.0 Hz), 103.6, 96.2, 83.6, 56.1, 45.3, 37.5, 33.3, 32.5, 27.1, 25.2, 23.1; IR (CHCl$_3$) 3032, 3005, 2934, 2863, 1604, 1512, 1452, 1235, 1101, 1013 cm$^{-1}$.

Further purification of 9b by HPLC (C-18, 2% water/methanol, 3 mL/min, 270 nm, Rt=6.3 min) afforded a white solid: m.p.=87–88° C.; $^1$H NMR (400 MHz, CDCl$_3$) δ 7.53 (m, 2H), 7.03 (m, 2H), 5.13 (d, J=1.2 Hz), 3.64 (s, 3H), 2.78 (ddd, J=14.4, 13.2, 3.6 Hz, 1H), 2.28 (ddd, J=14.4, 4.8, 3.2 Hz, 1H), 2.01–1.87 (m, 2H), 1.80–1.59 (m, 7H), 1.30 (dt, J$_d$=4.8 Hz, J$_t$=13.6 Hz, 1H), 1.21 (m, 1H); $^{13}$C NMR (100 MHz, CDCl$_3$) δ 162.8 (d, J=246 Hz), 136.7 (d, J=3.0 Hz), 127.2 (d, J=8.4 Hz), 115.0 (d, J=21.2 Hz), 105.1, 104.7, 83.7, 57.1, 47.4, 39.1, 35.6, 30.8, 26.8, 25.0, 23.8; IR (CHCl$_3$) 3034, 3012, 2934, 2863, 1604, 1512, 1447, 1235, 1139, 1106 cm$^{-1}$.

p-Fluoro-o-methylphenyl Ketone 4

To a solution of p-fluoro-o-methylphenyl bromide (506 µL, 4.02 mmol) in ether (12 mL) at −78° C. was added via syringe t-BuLi (2.5 mL, 1.50 M solution in pentane, 3.8 mmol) over 1 min. This solution was stirred at −78° C. for 1 h, at which time is was milky white. To this mixture was added dropwise via cannula r.t. solution of nitrile 1 (450 mg, 2.51 mmol) in ether (10 mL). The reaction immediately turned bright yellow. The mixture was stirred at −78° C. for 15 min then warmed to r.t. over 1 h and stirred at that temperature for 2 h. The reaction was then quenched with H$_2$O (3 mL) and diluted with ether (10 mL) and H$_2$O (10 mL). The organic phase was separated, and the aqueous phase was extracted with ether (50 mL×2). The organic portions were combined, washed with saturated aqueous NaCl, dried over anhydrous MgSO$_4$, filtered, and concentrated under reduced pressure. The crude product was purified by column chromatography (15 g short path, 1%→20% EtOAc/hexane) to give the desired product (476 mg, 1.64 mmol, 65%) as a pale yellow oil: $^1$H NMR (400 MHz, CDCl$_3$) δ 7.66 (m, 1H), 6.91 m, 2H), 5.77 (d, J=2.0 Hz, 1H), 3.38 (s, 3H), 2.82 (m, 3H), 2.50 (s, 3H), 1.98 (m, 2H), 1.80 (m, 1H), 1.72 (m, 3H), 1.64 (m, 1 H), 1.54 (m, 3H) 1.20 (m, 1H); $^{13}$C NMR (100 MHz, CDCl$_3$) δ 203.1, 163.6 (d, J=8.3 Hz), 140.4, 134.5 (d, J=3.1 Hz), 130.9 (d, J=9.1 Hz), 118.8, 118.4 (d, J=20.5 Hz), 112.2 (d, J=21.2 Hz), 59.0, 39.5, 32.5, 31.7, 28.2, 26.4, 25.8, 21.6, 21.5; IR (neat) 3067, 3001, 2928, 2853, 1686, 1604, 1583, 1448, 1238, 1124 cm$^{-1}$.

C$_3$-(p-Fluoro-o-methyl)phenyl Trioxanes 10 p-Fluoro-o-methylphenyl ketone 4 (230 mg, 0.792 mmol) was treated according to General Procedure 1 (irradiation for 20 min). The crude reaction mixture was purified by column chromatography (ca. 20 g Florisil®, 1%→20% EtOAc/hexanes) to give C$_{11\alpha}$-OMe trioxane 10a (40 mg, 0.12 mmol, 16%) and C$_{11\beta}$-OME trioxane 10b (50 mg, 0.16 mmol, 20%).

Further purification of 10a by HPLC (silica, 4% EtOAc/hexanes, 3 mL/min, 254 nm, rt=13.7 min) afforded a white solid: m.p.=112–113° C.; $^1$H NMR (400 MHz, CDCl$_3$) δ 7.68 (m, 1H), 6.84 (m, 2H), 5.17 (s, 1H), 3.53 (s, 3H), 2.96 (ddd, J=14.4, 12.8, 4.0 Hz, 1H), 2.46 (s, 3H), 2.42 (m, 1H), 2.10 (ddd, J=14.8, 4.4, 2.8 Hz, 1H), 1.89 (m, 1 H), 1.78–1.60 (m, 5H), 1.30–1.16 (m, 4H); $^{13}$C NMR (100 MHz, CDCl$_3$) δ 162.3 (d, J=246 Hz), 138.2 (d, J=7.6 Hz), 134.9 (d, J=3.1 Hz), 127.1 (d, J=8.3 Hz), 118.3 (d, J=21.2 Hz), 111.9 (d, J=20.4 Hz), 104.3, 95.9, 83.8, 55.8, 45.3, 36.9, 33.4, 32.5, 27.4, 25.3, 23.1, 21.3; IR (CHCl$_3$) 3031, 3004, 2934, 2863, 1612, 1592, 1495, 1451, 1264, 1240, 1100, 1016 cm$^{-1}$.

Further purification of 10b by HPLC (silica, 1% EtOAc/hexanes, 3 mL/min, 254 nm, R$_t$=10.4 min) afforded a white solid: m.p.=97–99° C.; $^1$H NMR (400 MHz, CDCl$_3$) δ 7.62 (m, 1H), 6.85 (m, 2H), 5.10 (d, J=0.8 Hz), 3.62 (s, 3H), 2.85 (ddd, J=14.4, 13.2, 3.6 Hz, 1H), 2.49 (s, 3H), 2.22 (ddd, J=14.8, 4.0, 4.0 Hz, 1H), 2.06–190 (m, 2H), 1H); $^{13}$C NMR (100 MHz, CDCl$_3$) δ 162.3 (d, J=246 Hz), 138.4 (d, J=8.4 Hz), 135.1 (d, J=3.1 Hz), 127.3 (d, J=8.4 Hz), 118.4 (d, J=20.5 Hz), 111.9 (d, J=19.7 Hz), 105.7, 104.6, 84.0, 57.1, 47.4, 38.3, 35.6, 30.7, 27.0, 25.0, 23.8, 21.5; IR (CHCl$_3$) 3034, 3009, 2934, 2862, 1613, 1591, 1495, 1447, 1270, 1244, 1105, 1021 cm$^{-1}$.

p-Methoxyphenyl Ketone 5

To a solution of p-methoxyphenyl bromide (336 μL, 2.68 mmol) in ether (6 mL) at −78° C. was added via syringe t-BuLi (1.8 mL, 1.40 M solution in pentane, 2.5 mmol). The resulting mixture was stirred for 30 min at −78° C., at which time a −78° C. solution of nitrile 1 (300 mg, 1.67 mmol) in ether (8 mL) was added via cannula. This mixture was stirred at −78° C. for 15 min, warmed to r.t. over 1 h, and stirred at this temperature for 4 h. The reaction was then quenched with H$_2$O (3 mL) and diluted with ether (20 mL) and H$_2$O (20 mL). The organic phase was separated, and the aqueous phase was extracted with ether (50 mL×2). The organic portions were combined, washed with saturated aqueous NaCl, dried over anhydrous MgSO$_4$, filtered, and concentrated under reduced pressure. The crude product was purified by column chromatography (15 g flash gel, 1%→20% EtOAc/hexane) to give the desired product (323 mg, 1.12 mmol, 67%) as a colorless oil: $^1$H NMR (400 MHz, CDCl$_3$) δ 7.93 (m, 2H), 6.92 (m, 2 H), 5.80 (d, J-1.6 Hz, 1H), 3.86 (s, 3H), 3.43 (s, 3H), 2.94–2.80 (m, 3H), 2.05–1.94 (m, 2H), 1.81 (M, 1H), 1.74 (m, 2H), 1.64 (m, 1H), 1.59–1.48 (m, 3H), 1.28–1.16 (m, 1H); $^{13}$C NMR (100 MNz, CDCl$_3$) δ 199.3, 162.9 140.2, 130.2, 130.0, 118.9, 13.4, 59.0, 55.2, 36.4, 32.6, 31.6, 28.2, 26.3, 25.9, 21.5; IR (neat) 3056, 3003, 2926, 2852, 1675, 1601, 1510, 1257, 1170, 1123 cm$^{-1}$.

C$_3$-(p-Methoxy)phenyl Trioxane 11 p-Methoxyphenyl ketone 5 (300 mg, 1.04 mmol) was treated according to General Procedure 1 (irradiation for 50 min). The crude reaction mixture was purified by column chromatography (ca. 30 g FLORISIL®, 1%→10% EtOAc/hexanes) to give trioxane 11 (140 mg, 0.437 mmol, 42%). The relative stereochemistry of this analog is ambiguous.

Further purification of 11 by HPLC (silica, 5% EtOAc/hexanes, 3 mL/min, 254 nm, Rt=19.0 min) afforded a white solid: m.p.=84.5–85° C.; $^1$H NMR (400 MHz, CDCl$_3$) δ 7.19 (m, 2H), 6.79 (m, 2H), 4.80 (s, 1H), 3.77 (s, 3H), 3.18 (s, 3H), 2.11 (m, 1H), 2.02–1.91 (m, 2H), 1.69 (m, 4H), 1.60 (m, 1H), 1.50–1.38 (m, 2H), 1.28 (m, 1H), 1.19–1.05 (m, 2H); $^{13}$C NMR (100 MHz, CDCl$_3$) δ 155.8, 146.1, 123.1, 120.8, 113.4, 99.5, 85.5, 55.4, 54.6, 39.9, 33.3, 30.2, 29.7, 25.7, 25.3, 22.8; IR (CHCl$_3$) 3029, 3012, 2938, 1506, 1450, 1342, 1180, 1202, 1129, 997 cm$^{-1}$; Anal. calcd for C$_{18}$H$_{24}$O$_5$; C 67.47, H 7.57, found: C 67.54, H 7.57. Note that this combustion analysis rules out the deoxytrioxane product, anal. calcd for C$_{18}$H$_{24}$O$_4$; C 71.02, H 7.96.

t-Butyldimethylsilyl-protected p-hydroxymethylphenyl Bromide

To a solution of p-bromobenzyl alcohol (p-hydroxymethylphenyl bromide, 1.00 g, 5.35 mmol) in CH$_2$Cl$_2$(50 mL) at 0° C. were added, both via syringe, 2,6-lutidine (930 μL, 8.02 mmol) and, 1 min later, (t-BuMe$_2$SiOTf) (1.6 mL, 7.0 mmol). The resulting solution was stirred for 1 h at 0° C. The reaction was then quenched with H$_2$O (3 mL) and diluted with ether (100 mL) and H$_2$O (100 mL). The organic phase was separated, and the aqueous phase was extracted with ether (100 mL×2). The organic portions were combined, washed with saturated aqueous NaCl, dried over anhydrous MgSO$_4$, filtered, and concentrated under reduced pressure. The crude product was purified by column chromatography (40 g short path, 1% EtOAc/hexane) to give the desired product (1.56 g, 5.16 mmol, 96%) as a colorless oil: $^1$H NMR (400 MHz, CDCl$_3$) δ 7.45 (m, 2H), 7.20 (m, 2H), 4.69 (s, 2H), 0.95 (d, J=0.8 Hz, 9H), 0.11 (d, J=0.8 Hz, 6H); $^{13}$C NMR (100 MHz, CDCl$_3$) δ 140.4, 131.2, 127.6, 120.5, 64.3, 25.9, 18.4, −5.2; IR (neat) 3028, 2929, 2885, 2857, 1593, 1487, 1471, 1257, 1087, 1012, 839, 778 cm$^{-1}$.

t-Butyldimethylsilyl-protected p-hydroxymethylphenyl Ketone 6

To a solution of the above aryl bromide (2.53 g, 8.37 mmol) in ether (25 mL) at −78° C. was added via syringe t-BuLi (5.2 mL, 1.50 M solution in pentane, 7.8 mmol). The resulting mixture was stirred at −78° C. for 45 min, at which time it was yellow and turbid. A r.t. solution of nitrile 1 (1.00 g, 5.58 mmol) in ether (25 mL) was then added via cannula. This reaction mixture was stirred at −78° C. for 15 min, warmed to r.t. over 1 h, and stirred at r.t. for 2 h. The reaction was then quenched with H$_2$O (3 mL) and diluted with ether (50 mL) and H$_2$O (50 mL). The organic phase was separated, and the aqueous phase was extracted with ether (100 mL×2). The organic portions were combined, washed with saturated aqueous NaCl, dried over anhydrous MgSO$_4$, filtered, and concentrated under reduced pressure. The crude product was purified by column chromatography (40 g flash gel, 1→10% EtOAc/hexane) to give the desired product (1.21 g, 3.00 mmol, 54%) as a colorless oil: $^1$H NMR (400 MHz, CDCl$_3$) δ 7.92 (m, 2H), 7.39 (m, 2H), 5.79 (d, J=1.6 Hz, 1H), 4.78 (s, 2H), 3.41 (s, 3H), 2.99–2.83 (m, 3H), 2.00 (m, 2H), 1.80 (m, 1H), 1.74 (m, 2H), 1.65 (m, 1H), 1.52 (m, 3H), 1.26–1.15 (m, 1H), 0.95 (s, 9H), 0.11 (s, 6H); $^{13}$C NMR (100 MHz, CDCl$_3$) δ 200.4, 146.3, 140.3, 136.0, 128.0, 125.6, 118.9, 64.4, 59.0, 36.8, 32.6, 31.6, 28.2, 26.4, 25.8, 21.6, 18.3, −5.3; IR (neat) 3055, 3001, 2928, 2856, 1684, 1609, 1462, 1256, 1124, 1094, 839, 778 cm$^{-1}$.

C$_3$-(p-hydroxymethyl)phenyl Trioxanes 12 t-Butyldimethylsilyl-protected p-hydroxy-methylphenyl ketone 6 (405) mg, 1.00 mmol) was treated according to General Procedure 1 (irradiation for 25 min). The crude reaction mixture was purified by column chromatography (ca. 30 g FLORISIL®, 1%→20% EtOAc/hexanes) to give a silylated C$_{11\alpha}$-OME trioxane (110 mg, 0.252 mmol, 25%) and a silylated C$_{11\beta}$-OMe trioxane (90 mg, 0.21 mmol, 21%). These trioxanes (100 mg, 0.230 mmol of C$_{11\alpha}$-OMe analog; 75 mg, 0.17 mmol of C$_{11\beta}$-OME analog) were individually desilylated according to General Procedure 2 (2 h for C$_{11\alpha}$-OMe analog; 3 h for C$_{11\beta}$-OMe analog). The resulting crude products were purified separately by column chromatography (ca. 10 g FLORISIL® each, 5%→50% EtOAc/hexanes) to give C$_{11\alpha}$-OMe trioxane 12a (60 mg, 0.19 mmol, 0.19 mmol, 83%) and C$_{11\beta}$-OMe trioxane 12b (40 mg, 0.12 mmol, 71%).

Further purification of 12a by HPLC (silica, 10% i-PrOH/hexanes, 3 mL/min, 254 nm, $R_t$=14.4 min) afforded a white solid: $^1$H NMR (400 MHz, CDCl$_3$) δ 7.54 (m, 2H), 7.34 (m, 2H), 5.18 (s, 1H), 4.68 (s, 2 H), 3.61 (s, 3H), 2.83 (ddd, J=14.4, 13.6, 4.0 Hz, 1H), 2.41 (m, 1 H), 2.26 (ddd, J=14.8, 4.8, 2.4 Hz, 1H), 1.89 (m, 1H), 1.82–1.69 (m, 5H), 1.67–1.56 (m, 1H), 1.33–1.15 (m, 4H); $^{13}$C NMR (100 MHz, CDCl$_3$) δ 141.4, 139.7, 126.5, 125.5, 103.8, 96.0, 83.6, 64.8, 55.9, 45.3, 37.5, 33.3, 32.5, 27.1, 25.2, 23.1; IR (CHCl$_3$) 3608, 3506, 3031, 3012, 2934, 2864, 1451, 1347, 1272, 1100, 1012, 972 cm$^{-1}$.

Further purification of 12b by HPLC (silica, 5% i-PrOH/hexanes, 3 mL/min, 254 nm, $R_t$=18.6 min) afforded a colorless oil: $^1$H NMR (400 MHz, CDCl$_3$) δ 7.55 (m, 2H), 7.35 (m, 2H), 5.14 (d, J=1.2 Hz, 1H), 4.69 (d, J=3.2 Hz, 2H), 3.65 (s, 3H), 2.78 (ddd, J=14.8, 13.2, 3.6 Hz, 1H), 2.29 (ddd, J=14.4, 4.4, 3.2 Hz, 1H), 2.02–1.89 (m, 2H), 1.81–1.59 (m, 8H), 1.30 (d$_t$, J$_d$=4.8 Hz, J$_t$=13.6 Hz, 1H), 1.20 (m, 1H); $^{13}$C NMR (125 MHz, CDCl$_3$) δ 141.4, 140.1, 126.7, 125.5, 105.1, 105.0, 83.8, 64.9, 57.1, 47.4, 39.1, 35.6, 30.8, 26.8, 25.0, 23.8; IR (CHCl$_3$) 3608, 3473, 3031, 3012, 2933, 2863, 1446, 1277, 1139, 1104, 1036, 960 cm$^{-1}$.

Further derivatives of trioxane 12b can be prepared according to the following scheme, as will be evident to persons of skill in the art.

The crude product was purified by column chromatography (20 g flash gel, 1%→20% EtOAc/hexane) to give the desired product (296 mg, 1.19 mmol, 43%) as a yellow oil: $^1$H NMR (400 MHz, CDCl$_3$) δ 7.56 (dd, J=1.6, 0.8 Hz), 7.15 (dd, J=3.6, 0.8 Hz), 6.51 (dd, J=3.6, 1.6 Hz), 5.79 (d, J=2.0 Hz), 3.44 (s, 3H), 2.86 (m, 1H), 2.83–2.70 (m, 2H), 1.99 (m, 2H), 1.81 (m, 1H), 1.73 (m, 2H), 1.73 (m, 2H), 1.63 (m, 1H), 1.52 (m, 3H), 1.20 (m, 1H); $^{13}$C NMR (100 MHz, CDCl$_3$) δ 190.0, 152.8, 145.9, 140.3, 118.9, 116.5, 111.9, 59.1, 36.8, 32.6, 31.5, 28.2, 26.4, 25.7, 21.6; IR (neat) 3133, 3001, 2926, 2853, 1677, 1569, 1469, 1240, 1202, 1124 cm$^{-1}$.

C$_3$-(2-Furyl) Trioxane 13

2-Furyl ketone 7 (250 mg, 1.01 mmol) was treated according to General Procedure 1 (irradiation for 35 min). The crude reaction mixture was purified by column chromatography (ca. 30 g FLORISIL®, 1%→20% EtOAc/hexanes) to give C$_{11\alpha}$-OMe trioxane 13 (45 mg, 0.16 mmol, 16%).

Further purification of 13 by HPLC (silica, 5% EtOAc/hexanes, 4 mL/min, 254 nm, $R_t$=14.2 min) afforded a white solid: m.p.=110.5–112° C.; $^1$H NMR (400 MHz, CDCl$_3$) δ 7.41 (dd, J=1.6, 0.8 Hz), 6.54 (dd, J=3.2, 0.8 Hz), 6.37 (dd, J=3.2, 1.6 Hz), 5.12 (s, 1H), 3.64 (s, 3H), 2.75 (ddd, J=14.8, 13.2, 3.6 Hz, 1H), 2.53 (ddd, J=14.8, 4.8, 2.8 Hz, 1H), 2.40 (m, 1H), 1.89 (m, 1H), 1.81–1.69 (m, 4H), 1.66–1.54 (M, Scheme Ia

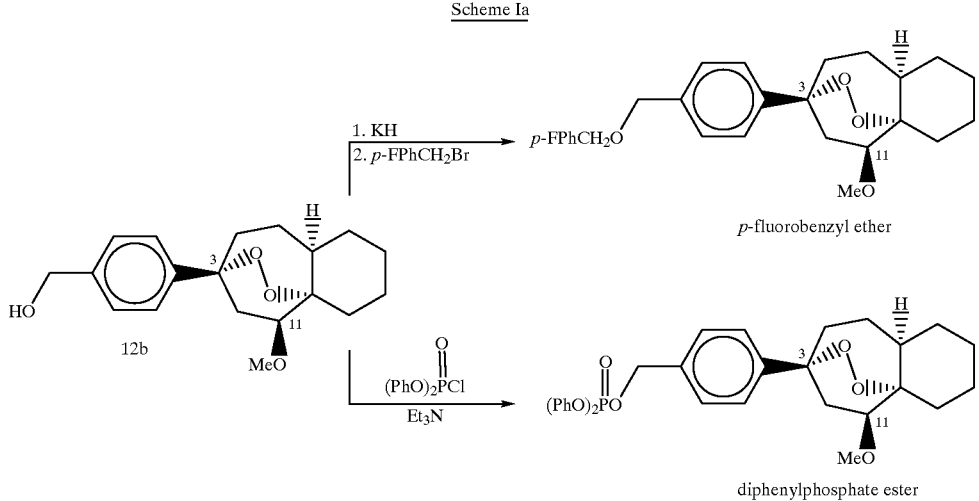

2-Furyl Ketone 7

To a solution of furan (525 μL, 7.25 mmol) in THF (8 mL) at 0° C. was added via syringe n-BuLi (5.6 mL, 1.25 M solution in hexanes, 7.0 mmol). The mixture was stirred at 0° C. for 12 h then warmed to r.t. and stirred for 1 h. This solution was then cooled back to 0° C. and a solution of nitrile 1 (500 mg, 2.79 mmol) in THF (4 mL) at 0° C. was added via cannula. The reaction immediately turned bright orange. After 5 min at 0° C., the mixture was warmed to r.t. and stirred for 6 h, at which time it was dark red. The reaction was then quenched with H$_2$O (3 mL) and then diluted with ether (20 mL) and H$_2$O (20 mL). The organic phase was separated, and the aqueous phase was extracted with ether (50 mL×2). The organic portions were combined, washed with saturated aqueous NaCl, dried over anhydrous MgSO$_4$, filtered, and concentrated under reduced pressure.

1H), 1.30–1.15 (m, 4H); $^{13}$C NMR (100 MHz, CDCl$_3$) δ 151.2, 143.2, 110.5, 109.3, 100.8, 96.4, 83.6, 55.8, 45.4, 34.1, 33.3, 32.5, 26.5, 25.3, 23.2; IR (CHCl$_3$) 3032, 3012, 2934, 2863, 1452, 1348, 1103, 1041, 941 cm$^{-1}$.

Syntheses of other compounds of the invention can be carried out by addition of particular substituents to common precursor molecules, as will be evident to persons of ordinary skill in the art.

Synthesis of C$_3$-Alkyl Trioxanes

C$_3$-alkyl trioxanes were synthesized according to the following general scheme:

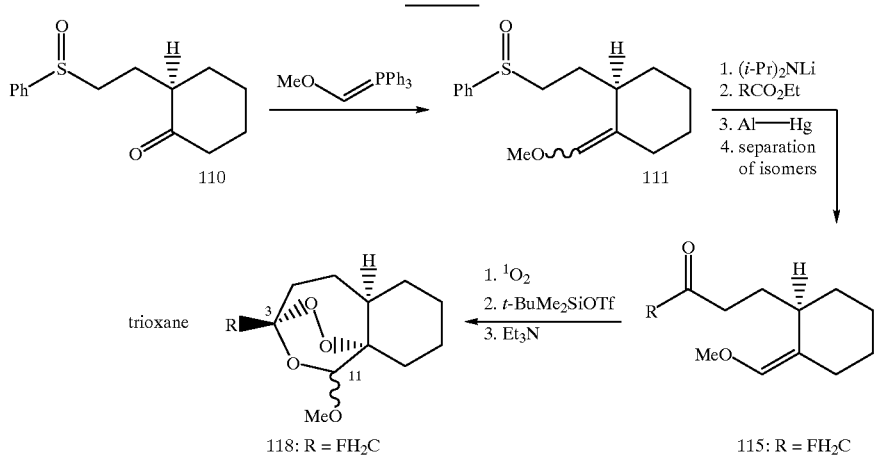

Scheme II

118: R = FH₂C      115: R = FH₂C

Sulfoxide Enol Ether 111

To a suspension of (methoxymethyl)triphenylphosphonium chloride (1.42 g, 4.14 mmol) in THF (15 mL) at −78° C. was added dropwise via syringe PhLi (2.34 mL, 1.77 M, 4.14 mmol). The resulting mixture was warmed to r.t. and stirred for 3 h. The resulting dark red solution was cooled to −78° C. and a solution of cyclohexanone sulfoxide 110 in THF (10 mL) was added dropwise by cannula. The resulting mixture was then allowed to warm to r.t. over 5 h, stirred for additional 5 h. At that time, the reaction was quenched with H₂O (25 mL), extracted with EtOAc, dried over anhydrous MgSO₄, and concentrated. Purification by column chromatography (flash gel, 50% EtOAc/hexane) afforded the desired sulfone enol ether 111 (644 mg, 2.32 mmol, 89%) as a roughly equal mixture of four diastereomers: $^1$H NMR (400 NMR (400 MHz, CDCl₃) δ 7.60 (m, 8H), 7.51 (m, 12H), 5.81 (s, 1H), 5.80 (s, 1H), 5.71 (s, 1H), 5.69 (s, 1H), 3.53 (s, 3H), 3.52 (s, 3H), 3.49 (s, 3H), 3.47 (s, 3H), 2.96 (m, 1H), 2.75 (m, 8H), 2.25 (m, 2H), 2.10–1.20 (m, 41H).

Fluoromethyl Ketone 115

To a solution of diisopropylamine (850 μL, 6.08 mmol) in dry THF (20 mL) at −78° C. was added dropwise via syringe n-BuLi (3.5 ML, 1.60 M in hexanes, 5.6 mmol) and the resulting mixture was stirred for 30 min. To this solution of lithium diisopropylamide was added dropwise by cannula a solution of sulfoxide enol ether 111 (1.41 g, 5.07 mmol) in THF (7 mL) at −78° C. The mixture was allowed to warm to −35° C. over 2 h, stirred for an additional hour, and then cooled back to −78° C. A solution of ethyl fluoroacetate (750 mg, 7.10 mmol) in THF (2 mL) was added via cannula. The resulting reaction mixture was stirred at −78° C. for 1 h and then allowed to warm to −35° C. over 2 h. After being stirred at that temperature for an additional 2 h, the reaction was quenched with saturated aqueous ammonium chloride (30 mL). The mixture was extracted with EtOAc, dried over anhydrous MgSO₄, and concentrated to give a crude acylated sulfoxide, which was directly used for the next step without purification.

Aluminum foil (1.37 g) was cut into small strips, submerged in an aqueous 2% mercury(II) chloride solution for 15 s, rinsed well first with absolute ethanol and then with diethyl ether. The resulting aluminum/mercury amalgam was snipped with scissors into a 0° C. solution of acylated sulfoxide (from above) in aqueous THF (90 mL, THF:H₂O=9:1). This reaction was stirred at 0° C. for 1.5 h. Anhydrous MgSO₄ was added to the resulting grey slurry and this mixture was filtered with copius ether rinses. The combined organic washes were concentrated to give the crude product, which was purified by column chromatography (flash gel, 90% EtOAc/hexane) to afford pure ketone 115 (286 mg, 1.33 mmol, 26%) and the corresponding E-enol ether contaminated with ca. 10% of ketone 115 (370 mg mixture, 1.72 mmol, 34%). Fluoromethyl ketone 115: $^1$H NMR (400 MHz, CDCl₃) δ 5.80 (d, J=2.0 Hz, 1H), 4.79 (d, J=47.6 Hz, 2H), 3.49 (s, 1H) 2.79 (m, 1H), 2.55–2.36 (m, 2H), 2.00–1.45 (m, 9H), 1.20 (m, 1H); $^{13}$C NMR (100 MHz, CDCl₃) δ 207.0 (d, J=18.2 Hz), 140.5, 118.6, 84.8 (d, J=184 Hz), 59.0, 36.1, 32.2, 31.6, 28.1, 26.2, 24.1, 21.5; IR (neat) 2928, 1738, 1677, 1233, 1124 cm$^{-1}$.

C₃-Fluoromethyl Trioxanes 118

Fluoromethyl ketone 115 (281 mg, 1.31 mmol) was treated according to General Procedure 1 (only 20 mL CH₂Cl₂, irradiation for 2 h). The crude reaction mixture was purified by column chromatography (flash gel, 90% EtOAc/hexanes) to give C₁₁α-OMe trioxane 118a (132 mg, 0.536 mmol, 41%) and C₁₁β-OMe trioxane 118b (17 mg, 0.069 mmol, 5%).

Trioxane 118a: m.p.=80–81° C.; $^1$H NMR (400 MHz, CDCl₃) δ 4.97 (s, 1H), 4.25 (d ABq, J$_{d(H—F)}$=47.2 Hz, ΔV$_{AB}$=18.7 Hz, J$_{AB}$=10.0 Hz, 2H), 3.52 (s, 3H), 2.35–2.22 (m, 1H), 2.12 (m, 1H), 1.85 (m, 2H), 1.75–1.60 (m, 7H), 1.34–1.15 (m, 2H); $^{13}$C NMR (100 MHz, CDCl₃) δ 104.8, 103.7 (d, J=19.8 Hz), 84.2, 83.8 (d, J=181 Hz), 57.2, 47.3, 35.4, 33.0, 30.8, 25.8, 24.9, 23.7.

Trioxane 118b: $^1$H NMR (400 MHz, CDCl₃) δ 5.01 (d, J=0.8 Hz, 1H), 4.24 (d ABq, J$_{d(H—F)}$=46.8 Hz, ΔV$_{AB}$=15.0 Hz, J$_{AB}$=10.0 Hz, 2H), 3.51 (s, 3H), 2.34 (m, 2H), 2.06 (m, 1H), 1.85 (m, 1H), 1.75–1.66 (m, 4H), 1.54–1.42 (m, 1H), 1.30–1.15 (m, 4H); $^{13}$C NMR (100 MHz CDCl₃) δ 102.5 (d, J=20.5 Hz), 84.4 (d, J=181 Hz), 95.5, 84.2, 55.6, 45.3, 33.2, 32.5, 31.5, 26.2, 25.2, 23.0.

C₃-Fluoroalkyl and C₃-Fluorophenyl 1,2,4-trioxanes can be prepared according to the following scheme:

13

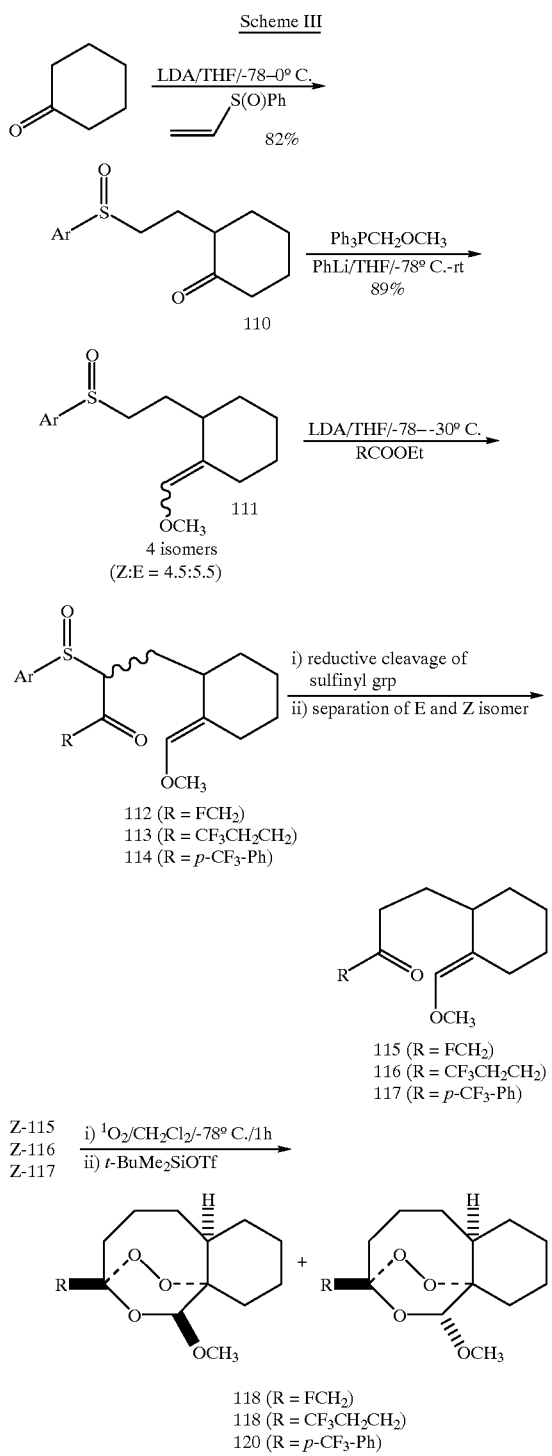

Scheme III 112 (R = FCH₂)
113 (R = CF₃CH₂CH₂)
114 (R = p-CF₃-Ph)

115 (R = FCH₂)
116 (R = CF₃CH₂CH₂)
117 (R = p-CF₃-Ph)

118 (R = FCH₂)
118 (R = CF₃CH₂CH₂)
120 (R = p-CF₃-Ph)

Ketophenyl Sulfoxide 110

To a solution of diisopropylamine (3.08 mL, 22 mmol) in dry THF (30 mL) was added dropwise 1.6M n-butyllithium (13.2 mL, 21 mmol) at −78° C. and the resulting solution was stirred for 30 min. To this LDA solution was added dropwise by cannula a solution of cyclohexanone (2.06 g, 21 mmol) in THF (30 mL) at −78° C. and the cooling bath was removed. After being stirred for 1 h, this solution was recooled to −78° C. A solution of phenyl vinyl sulfoxide (Aldrich, 3.34 g, 22 mmol) in THF (20 mL) was added, and the mixture was 4 allowed to reach rt over 5 h. Aqueous NaOH solution (1.0 N, 100 ml) was added, and the resulting mixture was stirred at rt for 1 h. The mixture was extracted with ethyl acetate, dried over anhydrous magnesium sulfate, and concentrated to give the crude product. Purification by silica gel chromatography (1:3=hexane:ethyl acetate) afforded 4.30 g (82%) of the desired keto phenyl sulfoxide 110 as inseparable mixture of the two diasteromers. ¹H NMR (400 MHz, CDCl₃); δ 1.30–2.55 (m, 11H), 2.72 (ddd,1H, J=5.2, 10.4, 12.8 Hz), 2.89–3.02 (m, 2H), 7.49–7.62 (m, 5H).

Ref. Montgomery, M. and Overman, L. E. J. Org. Chem. 1993, 58, 6476.

Methoxyvinyl Sulfoxide 111

To a suspension of methoxymethyl triphenylphosphonium chloride (1.42 g, 4.14 mmol) in dry THF (15 mL) at −78° C. was added dropwise a 1.77M phenyllithium solution (2.34 mL, 4.14 mmol), and the cooling bath was removed. Stirring was continued for 3 h to give a deep red solution. This solution was cooled to −78° C., and a solution of keto phenyl sulfoxide 110 in THF (10 mL) was added dropwise by cannula. The resulting mixture was then allowed to warm to rt over 5 h, stirred for an additional 5 h, and quenched with water (25 mL). The mixture was extracted with ethyl acetate, dried over anhydrous magnesium sulfate, and concentrated to give the crude product. Purification by silica gel chromatography (1:1=hexane:ethyl acetate) afforded 0.644 g (89%) of the desired product 111 as a mixture of the four diasteromers. ¹H NMR (400 MHz, CDCl₃); δ 1.20–2.98 (m, 13H), 3.47, 3.49, 3.52, 3.53 (s, 3H), 5.69, 5.71, 5.80, and 5.81 (br s, 1H), 7.22–7.66 (m, 5H).

Fluoromethyl Ketone 115

To a solution of diisopropylamine (0.85 mL, 6.08 mmol) in dry THF (2 mL) was added dropwise 1.6M n-butyllithium (3.50 mL, 5.58 mmol) at −78° C. and the resulting solution was stirred for 30 min. To this LDA soution was added dropwise by cannula a solution of sulfoxide 111 (1.41 g, 5.07 mmol) in THF (7 mL) at −78° C. The mixture was allowed to warm to −35° C. over 2 h, stirred at the same temperature for additional 1 h, and then cooled to −78° C. A solution of ethyl fluoroacetate ( 0.75 g, 7.10 mmol) in THF (2 ml) was added, and the reaction mixture was stirred at −78° C. for 1 h and then allowed to warm to −35° C. over 2 h. After being stirred at −35° C. for an additional 2 h, the reaction was quenched with a saturated ammonium chloride solution (30 mL). The mixture was extracted with ethyl acetate, dried over anhydrous magnesium sulfate, and concentrated to give the crude product 112, which was directly used for the next step without purification. The crude 112 obtained above was dissolved in 90 mL of aqueous THF solution (THF:H₂O= 9:1) and cooled to 0° C. A 1.37 g sample of aluminum foil was cut into small strips, submerged in aqueous 2% mercury (II) chloride solution for 15 sec, rinsed well with absolute ethanol and then diethyl ether. The resulting aluminum amalgam was snipped with scissors into the cold reaction mixture and stirring was continued at 0° C. for 1.5 h. Anhydrorous magnesium sulfate was added to the resulting gray slurry and the mixture was filtered off. The slurry was rinsed well with diethyl ether. The combined organic layer was concentrated to give the crude product, which was purified by silica gel chromatography (hexane:ethyl acetate= 10:1) to afford 0.286 g (26%) of the pure Z-115, along with 0.370 g (34%) of the corresponding E-isomer contaminated with ca. 10% of Z-115. Z115: $^1$H NMR (400 MHz, CDCl$_3$); δ 1.50–1.98 (m, 12H), 2.36–2.56 (m, 2H), 2.80 (m, 1H), 3.49 (s, 3H), 4.79 (d, 2H, JCH$_2$—F=47.6 Hz), 5.80 (d, 1H, J=2.0 Hz). $^{13}$C NMR (100 MHz, CDCl$_3$); δ 21.5, 24.1, 26.2, 28.1, 31.6, 32.2, 36.1, 59.0, 84.8 (d, JCH$_2$—F=184 Hz), 118.6, 140.5, 207.0 (d, JCO—F=18 Hz) IR(film); 2928, 1738, 1677, 1233, 1124 cm$^{-1}$. E-113: $^1$H NMR (400 MHz, CDCl3); δ 1.20–2.60 (m, 15H), 3.52 (s, 3H), 4.77 (d, 2H, JCH$_2$—F=47.6 Hz), 5.70 (s, IH). $^{13}$C NMR (100 MHz, CDC$_3$); δ 22.4, 22.8, 24.5, 27.1, 33.3. 36.5, 38.4, 59.3, 84.9 (d, JCH2—F=184 Hz), 119.4, 139.6, 207.2 (d, JCO—F=19 Hz).

Trifluoropropyl Ketone 116

Following the same procedure described for the preparation of 112, sulfoxide enol ether 111 (1.20 g, 4.32 mmol), diisopropylamine (0.72 mL, 5.16 mmol), n-butyl lithium (2.96 mL, 4.73 mmol of a 1.6M solution), and ethyl 4,4,4,-trifluorobutyrate (1.02 g, 6.02 mmol), were employed to produce, after purification by silica gel column chromatography (hexane:ethyl acetate=3:1), 0.495 g (29%) of an acylated product 113 as a mixture of diasteromers, along with 0.597 g of unreacted starting compound 111. The acylated product (0.470 g, 1.175 mmol) was treated with aluminum amalgam (prepared from aluminum foil) (0.317 g) and an aqueous 2% mercury (II) chloride solution) at 0° C. in aqueous THF (30 mL, THF:H$_2$O=9:1). Anhydrous magnesium sulfate was added to the resulting gray slurry and the mixture was filtered off. The mixture was then allowed to warm to rt over 2 h. The slurry was rinsed well with diethyl ether. The combined organic layer was concentrated to give the crude product, which was purified by silica gel chromatography (hexane:ethyl acetate=10:1) to afford 0.12 g (37%) of the pure Z-116, along with 0.15 g (46%) of the corresponding E-isomer. Z-116: 1H NMR (400 MHz, CDCl$_3$); δ 1.20–1.98 (m, 10H), 2.38 (m, 4H), 2.66 (m, 2H), 2.75 (m,1H), 3.48 (s, 3H), 4.79 (d, 2H, JCH$_2$—F=47.6 Hz), 5.80 (d, 1H, J=2.0 Hz). $^{13}$C NMR; δ 21.6, 25.2, 26.4, 27.9 (q, J=29.8 Hz), 28.2, 31.7, 32.3, 35.0 (q, J=2.2 Hz), 40.5, 59.1, 118.8, 127.0 (q, J=276.2 Hz), 140.4, 207.6. E-116:$^1$H NMR (400 MHz, CDCl3); δ 1.20–2.42(m, 15H), 2.67 (m,2H), 3.54 (s, 3H), 5.70 (s, IH). $^{13}$C NMR (100 MHz, CDCl$_3$); δ 22.4, 22.8, 25.4, 27.2, 27.9(q, J=29.6 Hz), 33.4, 35.0(q, J=2.3 Hz), 38.4, 41.1, 59.4, 119.5, 126.9 (q, J=274.6 Hz), 139.6, 207.2.

p-Trifluoromethylphenyl Ketone 117

Following the same procedure described for the preparation of 112, sulfoxide enol ether 111 (0.79 g, 2.84 mmol), diisopropylamine (0.48 ml, 3.41 mmol), n-butyllithium (1.95 mL, 3.12 mmol of a 1.6M solution), and methyl p-trifluoromethyl benzoate (0.75 g, 3.69 mmol) were employed to produce, after purification by silica gel column chromatography (hexane:ethyl acetate=3:1), 1.03 g (91%) of an acylated product 114 as a mixture of diasteromers. 114 (0.88 g, 1.955 mmol) was then dissolved in a 40 mL of THF-saturated NH$_4$Cl (1:1) solution and treated with activated zinc at rt. After being stirred for 2 h at rt, the reaction mixture was diluted with 40 mL of hexane-ethyl acetate (1:1) and washed with saturated sodium bicarbonated solution. The organic layer was dried over anhydrous magnesium sulfate and concentrated to give the crude product, which was purified by silica gel chromatography (hexane:ethyl acetate=15:1) to afford 0.121 g (19%) of the pure Z-117, along with 0.149 g (23%) of E-isomer contaminated ca. 15% of the correspondiUg Z isomer. Z-117: $^1$H NMR (400 MHz, CDCl$_3$); δ 1.21 (m, 1H), 1.53–2.07 (m, 9H), 2.85–3.02 (m, 3H), 3.38 (s, 3H), 5.77 (d, 1H, J=1.6 Hz), 7.70 (m, 2H), 8.03 (m, 2H). $^{13}$C NMR (100 MHz, CDCl$_3$); δ 21.7, 25.6, 26.4, 28.2, 31.7, 32.5, 37.1, 59.0, 118.8, 123.6 (q, J=273.2 Hz), 125.4 (q, J=3.8 Hz), 128.3, 133.9 (q, J=32.9 Hz), 140.0, 140.6, 199.7. E-116: $^1$H NMR (400 MHz, CDCl3); δ 1.15–2.02 (m, 9H), 2.30 (m,1H), 2.93 (m, 3H), 3.48 (s, 3H), 5.71 (s, 1H), 7.71 (2H, m), 8.03 (2H, m).

General Procedure: Trioxane Formation By Singlet Oxygenation

A sulfonation (3-necked) flask was fitted with a gas inlet line, an outlet line with stopcock, and a septum. To this flask was added solid methylene blue (ca. 5 mg) followed by a solution of the starting ketone (1.0 equivalent) in CH$_2$Cl$_2$ (0.01 M). The resulting solution was cooled to −78 ° C. while UHP oxygen passed through a drying column was bubbled (ca. 1 mL/s) through the solution. The reaction mixture was then irradiated with UV light (medium pressure Hg lamp) with continuous O$_2$ bubbling just until t.l.c. analysis showed >95% consumption of starting material. After irradiation, gaseous argon was introduced through the septum, the outlet stopcock was closed, and the gas inlet line was replaced with a stopper. To this reaction mixture, still at −78 ° C., was then added by cannula a −78° C. solution of t-BuMe$_2$SiOTf (1.1 equivalents) in CH$_2$Cl$_2$ (0.50 M). The resulting solution was stirred for 8 h at −78° C. At that time, the reaction was quenched by addition via syringe over 2 min of Et$_3$N (neat, 3.3 equivalents). The mixture was allowed to warm to room temperature (r.t.) slowly over at least 3 h and was then concentrated under reduced pressure to ca. 1 mL total volume.

C$_3$-Fluoromethyl Trioxanes 118

Fluoromethyl ketone Z-115 (281 mg, 1.31 mmol) was treated according to the general procedure (20 mL CH$_2$Cl$_2$, irradiation for 2 h). The crude product was purified by column chromatography (flash gel, 10% EtOAc/hexanes) to give C11α-OMe trioxane α-118 (132 mg, 41%) and C$_{11β}$-OMe trioxane β-118 (17 mg, 5%).
Trioxane α-118: m.p.=80–81° C.; $^1$H NMR (400 MHz, CDCl$_3$) δ 1.15–1.34 (m, 1H), 3.52 (s, 3H), 4.25 (d ABq, J d(H—F)=47.2 Hz, ΔVAB=18.7 Hz, J AB=10.0 Hz, 2H), 4.97(s, 1H),.; $^{13}$C NMR (100 MHz, CDCl$_3$) δ 23.7, 24.9, 25.8, 30.8, 33.0, 35.4, 47.3, 57.2, 83.8 (d, J=181 Hz), 84.2, 103.7 (d, J=19.8 Hz), 104.8.
Trioxane β-118: m.p.=75–76 ° C.; $^1$H NMR (400 MHz, CDCl$_3$) δ 1.15–1.30 (m, 4H), 1.42–1.54 (m, 1H), 1.66–1.75 (m, 4H), 1.85 (m, 1H), 2.06 (m, 1H), 2.34 (m, 2H), 3.51 (s, 3H), 4.24 (d ABq, J d(H—F)=46.8 Hz, ΔVAB=15.0 Hz, J AB=10.0 Hz, 2H), 5.01 (d, J=0.8 Hz, 1H); $^{13}$C NMR (100 MHz, CDCl$_3$) δ 23.0, 25.2, 26.2, 31.5, 32.5, 33.2, 45.3, 55.6, 84.2, 84.4 (d, J=181 Hz), 95.5, 102.5 (d, J=20.5 Hz). (note: The stereochemistry assignment of trioxanes 118 is ambiguous and needs to be confirmed)

C$_3$-Trifluoropropyl Trioxanes 119

Trifluoropropyl ketone Z-116 (105.6 mg, 0.38 mmol) was treated according to the general procedure (irradiation for 2 h). The crude reaction mixture was purified by column chromatography (flash gel, 10% EtOAc/hexanes) to give C$_{11β}$-OMe trioxane β-119 (36 mg, 31%) and C$_{11α}$-OMe trioxane α-119 (3.7 mg, 3%). β-119: $^1$H NMR (400 MHz, CDCl$_3$) δ 1.13–2.03 (m, 14H), 2.14–2.38 (m, 3H), 3.52 (s, 3H), 4.90 (s, 1H); $^{13}$C NMR (100 MHz, CDCl$_3$) δ 23.7, 25.0, 26.5, 27.7 (q, J=29.6 Hz), 30.8, 32.1 (q, J=2.3 Hz), 35.5, 36.9, 47.4, 57.1, 83.8, 104.3, 104.8, 127.0 (q, J=273.8 Hz).

α-119: ¹H NMR (400 MHz, CDCl₃) δ 1.15–1.56 (m, 5H), 1.65 (m, 4H), 1.81–2.01 (m, 4H), 2.21–2.41 (m, 4H), 3.55 (s, 3H), 4.96 (s, 1H); ¹³C NMR (100 MHz, CDCl₃,) δ 23.1, 25.2, 26.9, 27.8 (q, J=29.8 Hz), 32.17 (q, J=3.0 Hz), 32.4, 33.2, 35.6, 45.3, 56.1, 83.8, 95.8, 103.4. (Note: CF₃—carbon peak is missing, too weak to observe)

C₃-(p-Trifluoromethyl)phenyl Trioxanes 120 p-(Trifluoromethyl) phenyl ketone Z-117 (138 mg, 0.423 mmol) was treated according to the general procedure (irradiation for 2 h). The crude reaction mixture was purified by column chromatography (flash gel, 8% EtOAc/hexanes) to give $C_{11\beta}$-OMe trioxane β-120: m.p.=97–98° C.; ¹H NMR (400 mHz, CDCl₃) δ 1.17–1.81 (m, 9H), 1.83–2.20 (m, 2H), 2.23 (m, 1H), 2.77 (m, 1H), 3.66 (s, 3H), 5.14 (d, 1H, J=1.2 Hz), 7.64 (m, 4H).

α-120: m.p.=137–138° C.; ¹H NMR (400 MHz, CDCl₃) δ 1.59–1.94 (m, 10H), 2.19 (m, 1H), 2.42 (m, 1H), 2.83 (m, 1H), 3.59 (s, 3H), 5.19 (s, 1H), 7.64 (m, 4H).

Antimalarial Activity

The protozoan Plasmodium falciparum is a causative agent of malaria, the single most critical infectious disease of mankind. The antimalarial activity of the C₃-substituted trioxanes was determined according to the method of Desjardins et al. (13) as modified by Milhous et al. (14). Briefly, the antimalarial activity of the endoperoxides was tested in a tritiated-hypoxanthine incorporation assay by determining the concentration of the test compound needed to inhibit 50% of the incorporation of hypoxanthine by Plasmodium falciparum ($IC_{50}$) in human red blood cells.

Tables 1 and 2 present a tabulation of a number of compounds which have been synthesized along with the $IC_{50}$ (in nM).

TABLE 1

Antimalarial Activity of C₃-Aryl Trioxanes

| entry | Ar | trioxane | $C_{11}$—OMe | nM |
|---|---|---|---|---|
| 1 | biphenyl | 8a / 8b | α / β | t / 63[s] |
| 2 | F-phenyl | 9a / 9b | α / β | 80[s] / 30[e] |
| 3 | F-, Me-phenyl | 10a / 10b | α / β | 43[s] / 30[s] |
| 4 | MeO-phenyl | 11 | 1,2 | |
| 5 | HO-CH₂-phenyl | 12a / 12b | α / β | 15[s] |
| 6 | furyl | 13 | α[1] | 430[s] |
| 7 | thienyl | 14a / 14b | α / β | |
| 8 | quinolinyl | 15a / 15b | α / β | |
| 9 | phenyl | 16a / 16b | α / β | 110[e] / 38[e] |

[e]Expansion data (quadruplicate measurements resulting in highly accurate data).
[s]Survey data (one measurement).
[1]Only one trioxane product formed.
[2]Relative stereochemistry at all positions is ambiguous.

TABLE 2

Antimalarial Activity of C₃-Substituted Trioxanes

| entry | R | trioxane | $C_{11}$—OMe | nM |
|---|---|---|---|---|
| 1 | FH₂C— | 118a / 118b | α / β | 320[e] / 160[e] |
| 2 | CF₃CH₂CH₂— | 119a / 119b | α / β | 50[s] |
| 3 | F₃C-phenyl | 120a / 120b | α / β | |
| 4 | H₃C— | 121a / 121b | α / β | 960[e] |

[e]Expansion data (quadruplicate measurements resulting in highly accurate data).
[s]Survey data (one measurement).

It is particularly noted that in contrast to Artemisinin analogs (10), branched C₃ substituents in the structurally simplified trioxanes of the present invention can have increased potency, the potency of the $C_3$—$(CH_3)_2CHCH_2CH_2$ analog being increased by a factor of 5 over the $C_3$-methyl analog.

Activity Against Toxoplama gondii

Toxoplasma gondii is the causative agent of cerebral toxoplasmic encephalitis, an AIDS-related opportunistic infection. The biological activity of the compounds of the present invention can be measured against Toxoplasma gondii cultured in L929 cells.

More specifically, the cytotoxicity of the compounds can be tested in L929 cells by measuring the viability and replication of exposed cells. The cytotoxicity of the compound to the cultured cells can be measured using the MTT assay (Promega kit), according to the procedure of Carmichael et al. (15). MTT is an abbreviation for [3-(4,5-dimethylthiazol-2-yl)-2,5-dephenyltetrazolium bromide].

The inhibitory activity of the compounds can be tested by measuring the intracellular replication of T. gondii in infected L929 cells. The inhibition of the intracellular replication of T. gondii can be determined using the uracil incorporation assay (16).

While the invention has been described in connection with what is presently considered to be the most practical and preferred embodiments, it is to be understood that the invention is not to be limited to the disclosed embodiments, but on the contrary is intended to cover various modifications and equivalent arrangements included within the spirit and scope of the appended claims, including other anti-infective uses.

The following scientific articles and references have been cited throughout this application and the entire contents of each is hereby incorporated by reference.

REFERENCES

1. Jing-Ming, J., et al., *Acta Chim. Sinica* 37:129 (1979).
2. Schmid, G., et al., *J. Am. Chem. Soc.* 105:624 (1983).
3. Qinghaosu Antimalaria Coordinating Research Group, *Chinese Med. J.* 92:811 (1979).
4. Jiang, J. -B., et al., *Lancet* 2:285 (1982).
5. Bruce-Chwatt, L. J., *Brit. Med. J.* 284:767 (1982).
6. Luo, X. D., et al., *Med. Res. Rev.* 7:29–52 (1987).
7. Klayman, D. L., *Science* 228:1049–1054 (1985).
8. Koch, H., *Pharm. Int.* 2:184–185 (1981).
9. Posner et al. *Heteroatom Chemistry* 6:105–115 (1995)
10. Avery et al., *J. Med. Chem.* 39:2900–2906 (1996)
11. Kamchonwongpaisan et al., *Am. J. Trop. Med. Hyg.*, In press.
12. Posner et al. *J. Am. Chem. Soc.* 118:3537–3538 (1996).
13. Desjardins, R. E., et al., *Antimicrob. Agents Chemother.* 16:710–718 (1979).
14. Milhous, W. K., et al., *Antimicrob. Agents Chemother.* 27:525–530 (1985).
15. Carmichael, J., et al., *Cancer Res.* 47:936–942 (1987).
16. Fraser, D. C., et at., *Biochem. Biophys. Res. Comm.* 135:886–893 (1986).

What is claimed is:

1. A compound of the formula

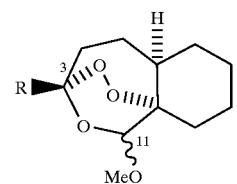

wherein R is selected from the group consisting of p-PhPh, p-FPh, p-F-o-MePh, p-MeOPh, p-(HOCH$_2$)Ph, p-formyl-Ph, p-diethylaminomethyl-Ph, and p-CF$_3$Ph.

2. A compound of the formula

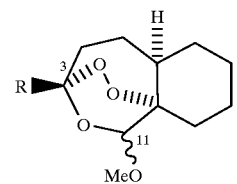

wherein R represents a substituted or unsubstituted heteroaryl group.

3. The compound of claim 2 wherein R represents furyl, thienyl or quinolyl.

4. The compound of claim 3 wherein R is selected from the group consisting of 2-furyl, 2-thienyl or 3-quinolyl.

5. A compound of the formula

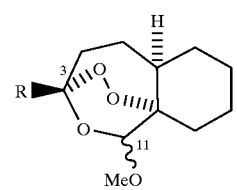

wherein R represents a fluoroalkyl group.

6. The compound of claim 5 wherein R is selected from the group consisting of fluoromethyl, trifluoromethyl, and (3,3,3)-trifluoropropyl.

7. A method for treating malaria comprising the step of administering a compound of formula

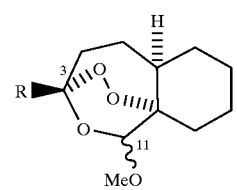

wherein R is a substituted phenyl group, to an individual afflicted with malaria.

8. A method for treating malaria comprising the step of administering a compound according to claim 1 to an individual afflicted with malaria.

9. A method for treating malaria comprising the step of administering a compound according to claim 2 to an individual afflicted with malaria.

10. A method for treating malaria comprising the step of administering a compound according to claim 3 to an individual afflicted with malaria.

11. A method for treating malaria comprising the step of administering a compound according to claim 4 to an individual afflicted with malaria.

12. A method for treating malaria comprising the step of administering a compound according to claim 5 to an individual afflicted with malaria.

13. A method for treating malaria comprising the step of administering a compound according to claim 6 to an individual afflicted with malaria.

* * * * *